United States Patent
Hartman et al.

(10) Patent No.: US 10,610,512 B2
(45) Date of Patent: Apr. 7, 2020

(54) MDI RELATED PRODUCTS AND METHODS OF USE

(71) Applicant: ISLAND BREEZE SYSTEMS CA, LLC, Oakland, CA (US)

(72) Inventors: Michael S. Hartman, Oakland, CA (US); James V. C. Boyles, Fairfield, CA (US)

(73) Assignee: Island Breeze Systems CA, LLC, Oakland, CA (US)

( * ) Notice: Subject to any disclaimer, the term of this patent is extended or adjusted under 35 U.S.C. 154(b) by 88 days.

(21) Appl. No.: 15/320,669

(22) PCT Filed: Jun. 16, 2015

(86) PCT No.: PCT/US2015/036033
§ 371 (c)(1),
(2) Date: Dec. 20, 2016

(87) PCT Pub. No.: WO2015/200049
PCT Pub. Date: Dec. 30, 2015

(65) Prior Publication Data
US 2017/0209409 A1    Jul. 27, 2017

Related U.S. Application Data

(60) Provisional application No. 62/017,762, filed on Jun. 26, 2014, provisional application No. 62/173,266, filed on Jun. 9, 2015.

(51) Int. Cl.
| | |
|---|---|
| *A61K 47/44* | (2017.01) |
| *A61M 15/00* | (2006.01) |
| *A61K 36/00* | (2006.01) |
| *A61K 31/352* | (2006.01) |
| *A61M 15/08* | (2006.01) |
| *A61K 31/05* | (2006.01) |
| *A61K 9/00* | (2006.01) |
| *A61K 47/10* | (2017.01) |
| *A61K 47/46* | (2006.01) |
| *A61M 11/00* | (2006.01) |

(52) U.S. Cl.
CPC ............ *A61K 31/352* (2013.01); *A61K 9/008* (2013.01); *A61K 31/05* (2013.01); *A61K 47/10* (2013.01); *A61K 47/44* (2013.01); *A61M 15/009* (2013.01); *A61M 15/08* (2013.01); *A61K 47/46* (2013.01); *A61M 11/001* (2014.02); *A61M 2202/0468* (2013.01); *A61M 2205/362* (2013.01)

(58) Field of Classification Search
None
See application file for complete search history.

(56) References Cited

U.S. PATENT DOCUMENTS

| | | |
|---|---|---|
| 3,156,614 A | 11/1964 | MacDonnell |
| 5,161,524 A | 11/1992 | Evans |
| 5,239,993 A | 8/1993 | Evans |
| 5,301,664 A | 4/1994 | Sievers et al. |
| 5,509,404 A | 4/1996 | Lloyd |
| 5,635,530 A | 6/1997 | Mechoulam et al. |
| 5,639,441 A | 6/1997 | Sievers et al. |
| 5,932,610 A | 8/1999 | Shohami et al. |
| 5,948,777 A | 9/1999 | Bender et al. |
| 6,060,069 A | 5/2000 | Hill et al. |
| 6,100,259 A | 8/2000 | Xiang et al. |
| 6,125,844 A | 10/2000 | Samiotes |
| 6,312,665 B1 | 11/2001 | Modi |
| 6,315,984 B1 | 11/2001 | Modi |
| 6,350,432 B1 | 2/2002 | Modi |
| 6,380,175 B1 | 4/2002 | Hussain et al. |
| 6,383,471 B1 | 5/2002 | Chen et al. |
| 6,383,513 B1 | 5/2002 | Watts et al. |
| 6,403,126 B1 | 6/2002 | Webster et al. |
| 6,509,005 B1 | 1/2003 | Peart et al. |
| 6,545,041 B2 | 4/2003 | Shohami et al. |
| 6,615,826 B1 | 9/2003 | Gabrio et al. |
| 6,630,121 B1 | 10/2003 | Sievers et al. |
| 6,630,507 B1 | 10/2003 | Hampson et al. |
| 6,682,716 B2 | 1/2004 | Hodges et al. |
| 6,703,015 B1 | 3/2004 | Solomon et al. |

(Continued)

FOREIGN PATENT DOCUMENTS

| | | |
|---|---|---|
| CA | 2382217 A1 | 3/2001 |
| CA | 2974208 A1 | 4/2017 |

(Continued)

OTHER PUBLICATIONS

Breathes, an electronic publication at www.westworld.com [retrieved on May 21, 2018]. Retrieved from the Internet: <URL:https://www.westword.com/news/highly-concentrated-tips-for-better-hash-from-colorados-best-5902203>. (Year: 2011).*

(Continued)

*Primary Examiner* — Robert T. Crow
*Assistant Examiner* — John P Nguyen
(74) *Attorney, Agent, or Firm* — Knobbe, Martens, Olson & Bear, LLP

(57) ABSTRACT

Provided herein are embodiments related to metered dose inhalers and formulations for such inhalers. In some embodiments, the inhalers are configured so as to allow a more comfortable experience for the subject receiving the formulation. In some embodiments, the formulation comprises various ingredients, such as terpenes and/or waxes, which can further enhance the level of comfort for the subject receiving the formulation.

19 Claims, 1 Drawing Sheet

(56) References Cited

U.S. PATENT DOCUMENTS

| | | |
|---|---|---|
| 6,703,418 B2 | 3/2004 | Plasse |
| 6,713,048 B2 | 3/2004 | Peart et al. |
| 6,747,058 B1 | 6/2004 | Dedhiya et al. |
| 6,810,873 B1 | 11/2004 | Haikarainen et al. |
| 6,946,150 B2 | 9/2005 | Whittle |
| 6,974,568 B2 | 12/2005 | Piomelli |
| 7,025,992 B2 | 4/2006 | Whittle et al. |
| 7,235,584 B2 | 6/2007 | Garzon et al. |
| 7,344,736 B2 | 3/2008 | Whittle et al. |
| 7,491,835 B2 | 2/2009 | Donevan et al. |
| 7,503,324 B2 | 3/2009 | Barney et al. |
| 7,595,397 B2 | 9/2009 | Zindell et al. |
| 7,612,181 B2 | 11/2009 | Wu et al. |
| 7,648,696 B2 | 1/2010 | McPhillips et al. |
| 7,709,536 B2 | 5/2010 | Whittle |
| 7,786,166 B2 | 8/2010 | Frey, II et al. |
| 7,807,711 B2 | 10/2010 | Korthout et al. |
| 7,968,594 B2 | 6/2011 | Guy et al. |
| 8,034,843 B2 | 10/2011 | Whittle et al. |
| 8,039,509 B2 | 10/2011 | Rossi et al. |
| 8,080,236 B2 | 12/2011 | Kordikowski et al. |
| 8,211,946 B2 | 7/2012 | Whittle |
| 8,222,292 B2 | 7/2012 | Goskonda et al. |
| 8,337,908 B2 | 12/2012 | Letzel et al. |
| 8,425,950 B1 | 4/2013 | Santillan et al. |
| 8,470,301 B2 | 6/2013 | Kordikowski et al. |
| 8,470,874 B2 | 6/2013 | Musty et al. |
| 8,476,312 B2 | 7/2013 | Rossi et al. |
| 8,481,085 B2 | 7/2013 | Musty et al. |
| 8,481,091 B2 | 7/2013 | Ross |
| 8,512,767 B2 | 8/2013 | Ross |
| 8,586,767 B2 | 11/2013 | Travis |
| D696,768 S | 12/2013 | Karlsson et al. |
| 8,603,515 B2 | 12/2013 | Whittle |
| 8,628,796 B2 | 1/2014 | Kottayil et al. |
| 8,629,177 B2 | 1/2014 | Castor et al. |
| 8,642,645 B2 | 2/2014 | Tanoue et al. |
| 8,662,381 B2 | 3/2014 | Kaar et al. |
| 8,753,696 B1 | 6/2014 | Lewis |
| 8,771,760 B2 | 7/2014 | Guy et al. |
| 8,809,261 B2 | 8/2014 | Elsohly et al. |
| 8,906,956 B2 | 12/2014 | Rossi et al. |
| 8,937,097 B2 | 1/2015 | Gutman et al. |
| 8,962,040 B2 | 2/2015 | Chong et al. |
| 8,980,940 B2 | 3/2015 | Rossi et al. |
| 8,980,941 B2 | 3/2015 | Hospodor |
| 8,980,942 B2 | 3/2015 | Stinchcomb et al. |
| 9,011,923 B2 | 4/2015 | Lewis et al. |
| 9,034,395 B2 | 5/2015 | Whittle et al. |
| 9,044,390 B1 | 6/2015 | Speir |
| 9,186,386 B2 | 11/2015 | Speir |
| 9,241,904 B1 | 1/2016 | Wu et al. |
| 9,717,683 B1 | 8/2017 | Eck et al. |
| 9,827,281 B2 | 11/2017 | Naheed |
| 9,827,282 B2 | 11/2017 | Naheed |
| 9,827,322 B2 | 11/2017 | Naheed |
| 9,895,321 B2 | 2/2018 | Sievers et al. |
| 9,918,961 B2 | 3/2018 | Hearn et al. |
| 10,231,948 B2 | 3/2019 | Nguyen |
| 2002/0004079 A1 | 1/2002 | Powell et al. |
| 2002/0031480 A1* | 3/2002 | Peart .................. A61K 9/008 424/45 |
| 2003/0066525 A1* | 4/2003 | Lewis .................. A61K 9/008 128/200.23 |
| 2003/0191180 A1 | 10/2003 | Ross |
| 2003/0203036 A1 | 10/2003 | Gordon et al. |
| 2003/0229027 A1* | 12/2003 | Eissens ............. A61K 9/1652 514/23 |
| 2004/0033280 A1* | 2/2004 | Whittle ............. A61K 31/352 424/774 |
| 2004/0034108 A1 | 2/2004 | Whittle |
| 2004/0062717 A1 | 4/2004 | Rosell et al. |
| 2004/0110827 A1 | 6/2004 | Aviv et al. |
| 2004/0139965 A1 | 7/2004 | Greenleaf et al. |
| 2004/0192760 A1 | 9/2004 | Whittle et al. |
| 2004/0223916 A1 | 11/2004 | Burt et al. |
| 2004/0248970 A1 | 12/2004 | Webster et al. |
| 2004/0258622 A1 | 12/2004 | Peart et al. |
| 2005/0061314 A1 | 3/2005 | Davies et al. |
| 2005/0070596 A1 | 3/2005 | Baker et al. |
| 2005/0079136 A1 | 4/2005 | Woolfe et al. |
| 2005/0123635 A1 | 6/2005 | McAughey et al. |
| 2005/0124668 A1 | 6/2005 | Deur et al. |
| 2005/0126562 A1 | 6/2005 | Rabinowitz et al. |
| 2006/0135599 A1 | 6/2006 | Symonds et al. |
| 2006/0165603 A1 | 7/2006 | Meakin et al. |
| 2006/0167084 A1 | 7/2006 | Dudley |
| 2006/0233721 A1 | 10/2006 | Tamarkin et al. |
| 2006/0258738 A1 | 11/2006 | Dieterich |
| 2007/0020193 A1 | 1/2007 | de Vries et al. |
| 2007/0060639 A1 | 3/2007 | Wermeling |
| 2007/0072938 A1 | 3/2007 | Rose |
| 2007/0072939 A1 | 3/2007 | Kupper |
| 2007/0099989 A1 | 5/2007 | Barbato |
| 2007/0104741 A1 | 5/2007 | Murty et al. |
| 2007/0161707 A1 | 7/2007 | Dooley et al. |
| 2007/0167514 A1 | 7/2007 | Moore, II et al. |
| 2007/0189979 A1 | 8/2007 | Zeng et al. |
| 2007/0293570 A1 | 12/2007 | Dooley et al. |
| 2008/0017191 A1 | 1/2008 | Davies et al. |
| 2008/0108647 A1 | 5/2008 | Travis |
| 2008/0112895 A1 | 5/2008 | Kottayil et al. |
| 2008/0119544 A1 | 5/2008 | Guy et al. |
| 2008/0159961 A1 | 7/2008 | Woolfe et al. |
| 2008/0175902 A1 | 7/2008 | Zajicek |
| 2008/0181942 A1 | 7/2008 | Zajicek |
| 2008/0255224 A1 | 10/2008 | Blum |
| 2009/0007905 A1 | 1/2009 | Vito |
| 2009/0068143 A1 | 3/2009 | Yacovan et al. |
| 2009/0181080 A1 | 7/2009 | Kottayil et al. |
| 2009/0197941 A1 | 8/2009 | Guy et al. |
| 2009/0247619 A1 | 10/2009 | Stinchcomb et al. |
| 2010/0008985 A1 | 1/2010 | Pellikaan et al. |
| 2010/0012118 A1 | 1/2010 | Storz |
| 2010/0016418 A1 | 1/2010 | Guy et al. |
| 2010/0022631 A1 | 1/2010 | Berry et al. |
| 2010/0035978 A1 | 2/2010 | Guy et al. |
| 2010/0196488 A1 | 8/2010 | Whittle |
| 2010/0258118 A1 | 10/2010 | Morton |
| 2010/0263663 A1* | 10/2010 | McGlasson ......... A61M 15/009 128/200.23 |
| 2010/0273895 A1 | 10/2010 | Stinchcomb et al. |
| 2010/0286098 A1 | 11/2010 | Robson et al. |
| 2010/0317729 A1 | 12/2010 | Guy et al. |
| 2010/0322852 A1 | 12/2010 | Merisko-Liversidge et al. |
| 2010/0322853 A1 | 12/2010 | Merisko-Liversidge et al. |
| 2010/0323038 A1 | 12/2010 | Ross |
| 2010/0329976 A1 | 12/2010 | Merisko-Liversidge et al. |
| 2011/0020244 A1* | 1/2011 | Flanders .............. A61K 9/0078 424/45 |
| 2011/0020448 A1 | 1/2011 | Park et al. |
| 2011/0021617 A1 | 1/2011 | Korthout et al. |
| 2011/0092583 A1 | 4/2011 | Murty et al. |
| 2011/0155130 A1 | 6/2011 | Barbato |
| 2011/0207718 A1 | 8/2011 | Bird |
| 2011/0311661 A1 | 12/2011 | Behr et al. |
| 2012/0010279 A1 | 1/2012 | Rossi et al. |
| 2012/0021075 A1 | 1/2012 | Umanskaya et al. |
| 2012/0045479 A1 | 2/2012 | Sievers et al. |
| 2012/0095087 A1 | 4/2012 | Hyatt |
| 2012/0107300 A1 | 5/2012 | Schirripa |
| 2012/0207685 A1 | 8/2012 | Vega et al. |
| 2012/0252885 A1 | 10/2012 | Barbato |
| 2012/0264818 A1 | 10/2012 | Newland |
| 2012/0289589 A1 | 11/2012 | Travis |
| 2012/0304990 A1 | 12/2012 | Todd |
| 2012/0309820 A1 | 12/2012 | Zurier et al. |
| 2013/0012575 A1 | 1/2013 | Letzel et al. |
| 2013/0104881 A1 | 5/2013 | Toneguzzo et al. |
| 2014/0039043 A1 | 2/2014 | Musty et al. |
| 2014/0100269 A1 | 4/2014 | Goskonda et al. |
| 2014/0248379 A1 | 9/2014 | Mueller |
| 2014/0271940 A1 | 9/2014 | Wurzer |

(56) References Cited

U.S. PATENT DOCUMENTS

| | | |
|---|---|---|
| 2014/0287068 A1* | 9/2014 | Lewis .................... A01G 22/00 424/725 |
| 2014/0328938 A1 | 11/2014 | Miller et al. |
| 2014/0357708 A1 | 12/2014 | Murty |
| 2015/0044315 A1 | 2/2015 | Letzel et al. |
| 2015/0057341 A1 | 2/2015 | Perry |
| 2015/0072020 A1 | 3/2015 | Young et al. |
| 2015/0086494 A1 | 3/2015 | Sekura et al. |
| 2015/0105455 A1 | 4/2015 | Bjorncrantz |
| 2015/0126595 A1 | 5/2015 | Smith |
| 2015/0126596 A1 | 5/2015 | Gutman et al. |
| 2015/0132400 A1 | 5/2015 | De Vries et al. |
| 2015/0231108 A1 | 8/2015 | Hearn et al. |
| 2015/0265720 A1 | 9/2015 | Levine et al. |
| 2015/0297653 A1 | 10/2015 | Speier |
| 2016/0058866 A1 | 3/2016 | Sekura et al. |
| 2016/0228385 A1 | 8/2016 | Sievers et al. |
| 2017/0021025 A1 | 1/2017 | Naheed |
| 2017/0056368 A1 | 3/2017 | Hearn et al. |
| 2017/0135984 A1 | 5/2017 | Solomon |
| 2017/0157343 A1 | 6/2017 | Davidson et al. |
| 2017/0216538 A1 | 8/2017 | Kinsey et al. |
| 2017/0281701 A1 | 10/2017 | Kan |
| 2017/0304564 A1 | 10/2017 | DeHaan et al. |
| 2017/0304567 A1 | 10/2017 | Adelson |
| 2018/0000731 A1 | 1/2018 | Eck et al. |
| 2018/0104214 A1 | 4/2018 | Raichman |
| 2018/0133272 A1 | 5/2018 | Crowley |
| 2018/0140787 A1 | 5/2018 | Hartman |
| 2018/0344634 A1 | 12/2018 | Eck et al. |
| 2018/0360772 A1 | 12/2018 | Eck et al. |

FOREIGN PATENT DOCUMENTS

| | | |
|---|---|---|
| CN | 101198324 B | 6/2011 |
| EP | 1340492 A1 | 9/2003 |
| EP | 2207528 B1 | 10/2013 |
| JP | 2008536881 A | 9/2008 |
| WO | WO 2000/024362 A2 | 5/2000 |
| WO | WO 01/89589 A1 | 11/2001 |
| WO | WO 2003/006010 A1 | 1/2003 |
| WO | WO 2003/037306 A3 | 5/2003 |
| WO | WO 2003055549 A1 | 7/2003 |
| WO | WO 2005/055985 A1 | 6/2005 |
| WO | WO 2005/079771 A1 | 9/2005 |
| WO | WO 2008/021451 A2 | 2/2008 |
| WO | WO 2009/043395 A2 | 4/2009 |
| WO | WO 2010/020666 A2 | 2/2010 |
| WO | WO 2012/050945 A1 | 4/2012 |
| WO | WO 2013/002844 A1 | 4/2013 |
| WO | WO 2013/130767 A1 | 9/2013 |
| WO | WO 2004/000290 A1 | 12/2013 |
| WO | WO 2015/195711 A9 | 12/2015 |
| WO | WO 2015/200049 A1 | 12/2015 |
| WO | WO 2016/187156 A1 | 11/2016 |
| WO | WO 2017/118980 A1 | 7/2017 |
| WO | WO 2017/182976 A1 | 10/2017 |

OTHER PUBLICATIONS

Lewis, an electronic article in www.buzzfeed.com [retrieved on May 21, 2018]. Retrieved from the Internet: <URL: https://www.buzzfeed.conn/amandachicagolewis/is-hash-oil-safe?utm_term=.ck8krNqyl#.kj5n5mwx8>. (Year: 2015).*

Meehan-Atrash, "Toxicant Formation in Dabbing: The Terpene Story", ACS Omega, 2, 6112-6117 (Year: 2017).*

Hendriks, "Alkanes of the Essential Oil of *Cannabis sativa*", Phytochemistry, vol. 16, pp. 719-721, 1977 (Year: 1977).*

International Search Report and Written Opinion, dated Sep. 8, 2015, in International Application No. PCT/US2015/036033.

International Preliminary Report on Patentability, dated Jan. 5, 2017, in International Application No. PCT/US2015/036033.

International Search Report and Written Opinion, dated Oct. 4, 2016, in International Application No. PCT/US2016/032777.

Newman, S. P., Principles of Metered-Dose Inhaler Design, Respiratory Care, vol. 50, No. 9, pp. 1177-1190, 2005.

U.S. Appl. No. 61/899,781, filed Nov. 4, 2013, Hartman.

Office Action dated Oct. 4, 2018 in Canadian Patent Application No. 2, 952, 934.

Extended European Search Report dated Feb. 6, 2018 in European Patent Application No. 15811425.6.

International Preliminary Report on Patentability dated Nov. 21, 2017 in International Patent Application No. PCT/US2016/032777.

Myrtha Naef et al: "Development and pharmacokinetic characterization of pulmonal and intravenous delta-9-tetrahydrocannabinol (THC) in humans", Journal of Pharmaceutical Sciences, American Pharmaceutical Association, Washington, US, vol. 93, No. 5, May 1, 2004 (May 1, 2004), pp. 1176-1184, XP008140183, ISSN: 0022-3549, [retrieved on 20040223], DOI: 10.1002/JPS.20037.

Notice of Allowance dated Jul. 17, 2018 in Australian Patent Application No. 2015280412.

Office Action dated Jan. 23, 2017 in Jamaican Patent Application No. 18/1/5741.

Office Action dated Aug. 22, 2017 in Australian Patent Application No. 2015280412.

Office Action dated Dec. 27, 2017 in Canadian Patent Application No. 2,952,934.

Office Action dated Mar. 13, 2018 in Australian Patent Application No. 206263444.

Partial European Search Report dated Dec. 7, 2018 in European Patent Application No. 16797119.1.

Office Action dated Jul. 22, 2019 in Canadian Patent Application No. 2, 952, 934.

Extended European Search Report dated Apr. 2, 2019 in European Patent Application No. 16797119.1.

Examination Report in corresponding Australian Application No. 2018253527, dated May 15, 2019.

* cited by examiner

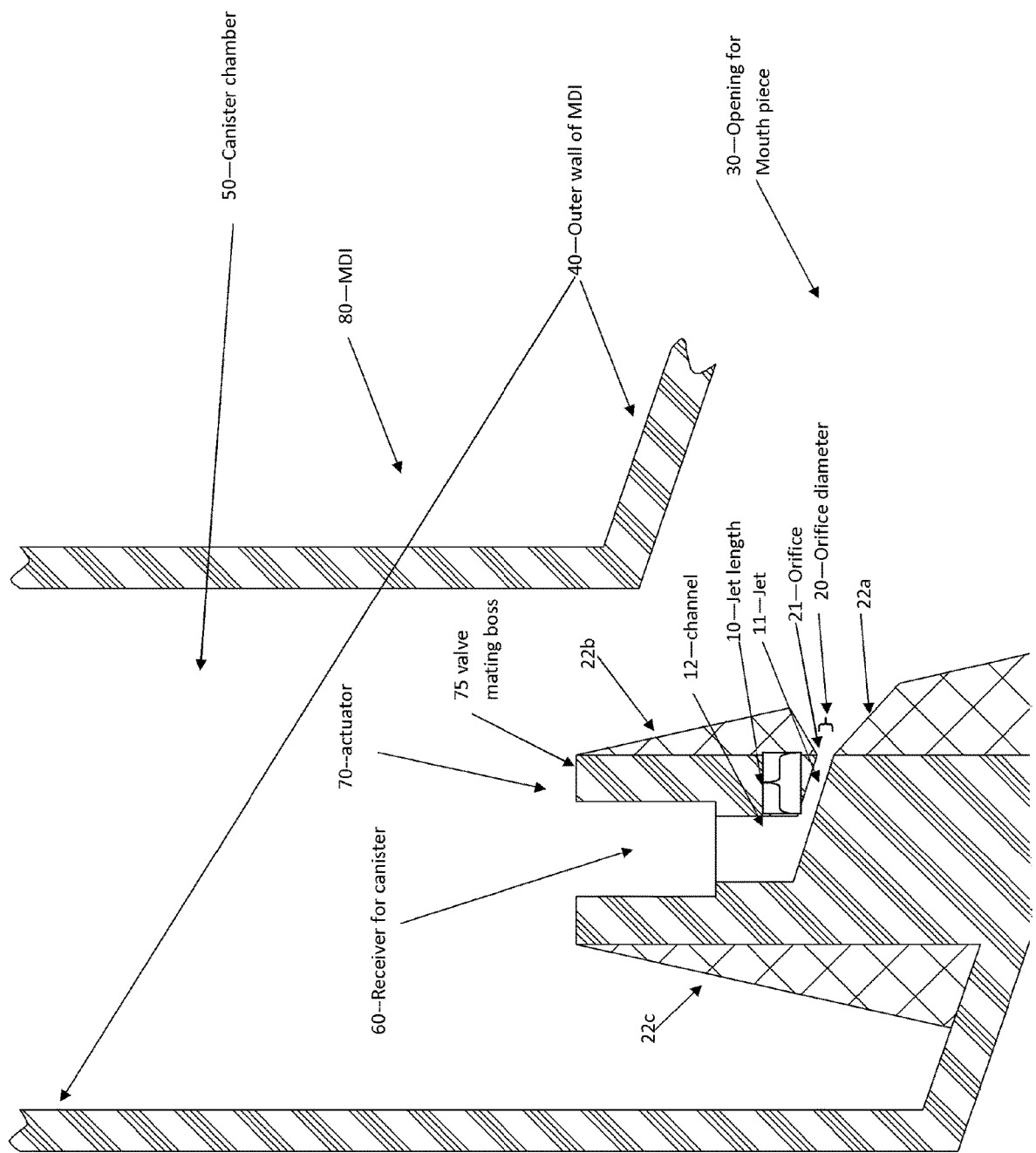

MDI RELATED PRODUCTS AND METHODS OF USE

PRIORITY AND CROSS REFERENCE TO RELATED APPLICATIONS

This application is the U.S. National Phase Application under 35 U.S.C. § 371 of International Application No. PCT/US2015/036033, filed Jun. 16, 2015, designating the U.S. and published in English as WO 2015/200049A1 on Dec. 30, 2015, which claims the benefit of U.S. Provisional Application No. 62/017,762, filed Jun. 26, 2014, and U.S. Provisional Application No. 62/173,266, filed Jun. 9, 2015. Any and all applications for which a foreign or a domestic priority is claimed is/are identified in the Application Data Sheet filed herewith and is/are hereby incorporated by reference in their entirety under 37 C.F.R. § 1.57.

BACKGROUND OF THE INVENTION

Generally speaking, formulations and devices for metered dose inhalers have historically been optimized and or improved for the ability to deliver a maximal amount of a formulation with specific characteristics.

Field of the Invention

The present application relates to metered dose inhaler related products, formulations, and methods of manufacturing.

SUMMARY OF THE INVENTION

In some embodiments, a formulation for metered dose inhalation is provided. The formulation can comprise an amount of at least one cannabinoid, an amount of a propellant suitable for metered dose inhalation application to a human subject, a polar solvent miscible with the propellant; the cannabinoid(s), and an amount of a wax and/or terpene.

In some embodiments, a formulation for metered dose inhalation is provided. The formulation can comprise an amount of an activated cannabinoid, wherein the activated cannabinoid comprises at least Tetrahydrocannabinol (THC) and Cannabidiol (CBD), and an amount of ethanol sufficient to serve as a solvent, an amount of a propellant, wherein the propellant is at least one of 1,1,1,2-Tetrafluoroethane (HFA 134a) and 1,1,1,2,3,3,3-Heptafluoropropane (HFA 227). The formulation can further comprise at least one of: a) an amount of a wax, wherein the amount of wax is at least sufficient to provide a higher level of comfort to a subject receiving a dose from a metered dose inhaler that is administering the formulation, and wherein the wax comprises a wax that naturally occurs in a cannabis plant, or b) an amount of a natural terpene, wherein the natural terpene is one that is present in a cannabis plant. The amount of the natural terpene is at least sufficient to provide a higher level of comfort to a subject receiving a dose from a metered dose inhaler that is administering the formulation.

In some embodiments, the formulation can comprise an amount of an activated cannabinoid, wherein the activated cannabinoid comprises at least Tetrahydrocannabinol (THC), tetrahydrocannabivarin (THCV), and Cannabidiol (CBD), and an amount of ethanol sufficient to serve as a solvent, an amount of a propellant, wherein the propellant is at least one of 1,1,1,2-Tetrafluoroethane (HFA 134a) and 1,1,1,2,3,3,3-Heptafluoropropane (HFA 227). The formulation can further comprise at least one of: a) an amount of a wax, wherein the amount of wax is at least sufficient to provide a higher level of comfort to a subject receiving a dose from a metered dose inhaler that is administering the formulation, and wherein the wax comprises a wax that naturally occurs in a cannabis plant, or b) an amount of a natural terpene, wherein the natural terpene is one that is present in a cannabis plant. The amount of the natural terpene is at least sufficient to provide a higher level of comfort to a subject receiving a dose from a metered dose inhaler that is administering the formulation.

In some embodiments, a method for preparing a formulation is provided. The method can comprise providing a source of a cannabinoid, obtaining an active ingredient from the source by carbon dioxide extraction, combining the active ingredient with a polar solvent to obtain a mixture, heating the mixture to solubilize into a solvent, cooling the solvent to thereby obtain a gel or viscous liquid, and solubilizing the gel or viscous liquid with HFA.

In some embodiments, a method for preparing a formulation is provided. The method can comprise providing a source of a cannabinoid, obtaining an active ingredient from the source by butane and/or organic solvent extraction, combining the active ingredient with a polar solvent to obtain a mixture, heating the mixture to solubilize into a solvent, cooling the solvent to thereby obtain a gel or viscous liquid, and solubilizing the gel or viscous liquid with HFA.

In some embodiments, a metered dose inhaler canister is provided. The canister can comprise a formulation according to any of those provided herein, and a coating over an interior surface of the canister, wherein the coating comprises at least one of anodized aluminum or a fluoropolymer.

In some embodiments, a metered dose inhaler is provided. The MDI can comprise a formulation as provided herein and an actuator drug/propellant pathway. The actuator can comprise an actuator orifice cylinder configured to provide an appropriate mean mass aerosol diameter (MMAD) particulate size distribution (between 0.5 and 5.0 micron, in some embodiments this can be as determined by the guidance set forth in the United States Pharmacopeia in chapter <601>) of the formulation, and of sufficient surface area and heat sink properties to provide for single and rapid dispensing cycles of the formulation (including propellant) to maintain dose content uniformity, particle size distribution, and the comfort of the patient. The actuator orifice cylinder is configured by at least one of: a) an appropriate surface area, internal geometry jet length or shape, surface texture, or material of the actuator orifice cylinder; or b) an increased mass of the external geometry of the actuator orifice cylinder to act as a heat sink by at least 5% additional mass.

In some embodiments, an amount of an extract from a cannabinoid containing plant is provided. The extract can comprise a) an activated cannabinoid, wherein the activated cannabinoid comprises at least Tetrahydrocannabinol (THC) and Cannabidiol (CBD), and b) at least one of: i) an amount of a wax, wherein the amount of wax is at least sufficient to provide a higher level of comfort to a subject receiving a dose from a metered dose inhaler that is administering the formulation, and wherein the wax comprises a wax that naturally occurs in a cannabis plant, or ii) an amount of a natural terpene, wherein the natural terpene is one that is present in a cannabis plant, and wherein the amount of the natural terpene is at least sufficient to provide a higher level of comfort to a subject receiving a dose from a metered dose inhaler that is administering the formulation. The extract can further include an amount of a polar solvent, and an amount of a HFA propellant. The propellant is at least one of 1,1,1,2-Tetrafluoroethane (HFA 134a) and 1,1,1,2,3,3,3-Heptafluoropropane (HFA 227). The extract:polar solvent:HFA propellent is in a ratio ranging from 0.5:0.5:99 to 30:30:40.

In some embodiments, an amount of an extract from a cannabinoid containing plant is provided. The extract can comprise a) an activated cannabinoid, wherein the activated cannabinoid comprises at least Tetrahydrocannabinol (THC), tetrahydrocannabivarin (THCV), and Cannabidiol (CBD), and b) at least one of: i) an amount of a wax, wherein the amount of wax is at least sufficient to provide a higher level of comfort to a subject receiving a dose from a metered dose inhaler that is administering the formulation, and wherein the wax comprises a wax that naturally occurs in a cannabis plant, or ii) an amount of a natural terpene, wherein the natural terpene is one that is present in a cannabis plant, and wherein the amount of the natural terpene is at least sufficient to provide a higher level of comfort to a subject receiving a dose from a metered dose inhaler that is administering the formulation. The extract can further include an amount of a polar solvent, and an amount of a HFA propellant. The propellant is at least one of 1,1,1,2-Tetrafluoroethane (HFA 134a) and 1,1,1,2,3,3,3-Heptafluoropropane (HFA 227). The extract:polar solvent:HFA propellent is in a ratio ranging from 0.5:0.5:99 to 30:30:40.

BRIEF DESCRIPTION OF THE DRAWINGS

FIG. 1 depicts a cross-sectional diagram of a metered dose inhaler indicating the jet length and orifice diameter that can be adjusted as described in some embodiments herein.

DETAILED DESCRIPTION OF THE PREFERRED EMBODIMENT

Provided herein are devices and formulations that provide or result in a more comfortable subject experience when a metered dose inhaler is used to administer a formulation. In some embodiments, the formulation and/or device and/or method delivers more than 1 mg of extract per actuation with the ratio of extract to ethanol greater than 15% for superior subject comfort.

In some embodiments, a formulation for metered dose inhalation is provided. The formulation can comprise an amount of at least one cannabinoid, an amount of a propellant suitable for metered dose inhalation application to a human subject, a polar solvent miscible with the propellant, a cannabinoid(s), and an amount of a wax. It has been discovered that the addition of a wax and/or a terpene to the formulation can result in a greater level of comfort for a subject receiving the formulation.

In some embodiments, the wax can be any type of wax. In some embodiments, the wax is a natural wax. The wax can comprise a plant based natural wax. The plant based natural wax can comprise a cannabis wax. In some embodiments, the plant based natural wax can comprise a non-cannabis wax. In some embodiments, the cannabis wax can include one or more of a straight chain paraffins such as nonacosane (C29), heptacosane (C27) or hentriacontane (C31), or branched chained parafins such as isononacosane, isoheptacosane or isohentriacontane.

In some embodiments, the formulation can further (or instead) comprise at least one terpene. In some embodiments, any type of terpene can be employed. In some embodiments, the amount of the terpene is at least 3 mcg/mL and less than 100 mg/mL. In some embodiments, the terpene is selected from the group of at least one of: Pinene, Limonene, Myrcene, Phellandrene, Carene, Terpinene, Linalool, Fenchol, Borneol, Terpineol, Geraniol, Humulene, Caryophyllene, Bisabolol or Phytol. In some embodiments, the terpene is selected from the group of at least one of: Pinene, Limonene, Myrcene, Phellandrene, Carene, Terpinene, Linalool, Fenchol, Borneol, Terpineol, Geraniol, Humulene, Caryophyllene, Caryophyllene Oxide, Bisabolol, Citronellol, Menthol, Ocimene, Camphene or Phytol.

In some embodiments, the amount of the at least one cannabinoid is sufficient for the desired purpose (for example achieving great subject comfort). In some embodiments, the amount of the at least one cannabinoid is at least 0.2 mg/mL and less than 350 mg/mL, for example 0.5 to 300 mg/mL, 1 to 200 mg/mL, 10 to 100, or 30 to 60 mg/mL.

In some embodiments, the cannabinoid employed can be 100% activated. In some embodiments, less than 100% of the cannabinoid present is activated, for example, less than 100%, 99, 98, 95, 90, 80, 70, 50, 40, 30, 20, 10, or 5% or less of the cannabinoid present can be activated. In some embodiments, at least 50% of the cannabinoid is activated, for example, at least 50, 60, 70, 80, 90, 95, 96, 97, 98, or 99 percent of the cannabinoid is activated. In some embodiments, none of the cannabinoid is activated. In some embodiments the at least one cannabinoid comprises at least one activated cannabinoid, such as 2, or more different cannabinoids are activated and/or at least partially activated.

The term "cannabinoid" as used herein denotes a class of diverse chemical compounds that act on cannabinoid receptors on cells that repress neurotransmitter release in the brain. The class includes endocannabinoids, phytocannabinoids, and synthetic cannabinoids. Examples include cannabis-derived cannabindoids, delta-nine-tetrahydrocannabinol (THC) and cannabidiol (CBD), Cannabigerol-type, Cannabichromene-type, Tetrahydrocannabinol- and Cannabinol-type, Cannabielsoin-type, iso-Tetrahydrocannabinol-type, Cannabicyclol-type, and Cannabicitran-type. In some embodiments, cannabinoid includes: CBG (Cannabigerol), CBC (Cannabichromene), CBL (Cannabicyclol), CBV (Cannabivarin), THCV (Tetrahydrocannabivarin), CBDV (Cannabidivarin), CBCV (Cannabichromevarin), CBGV (Cannabigerovarin), and/or CBGM (Cannabigerol Monomethyl Ether).

In some embodiments, the at least one cannabinoid can be at least one of tetrahydrocannabinol (THC), cannabidiol (CBD), and tetrahydrocannabivarin (THCV). In some embodiments, the at least one cannabinoid comprises both THC and CBD.

In some embodiments, the formulation further comprises at least one terpene. In some embodiments, in addition to the at least one terpene noted above, the formulation comprises at least one activated cannabinoid. In some embodiments, the at least one terpene comprises at least caryophyllene. In some embodiments, the at least one terpene is present in an amount of at least about 3 mcg/mL, for example, at least 4, 5, 6, 7, 8, 9, 10, 20, 30, 40, 50 or more mcg/mL.

In some embodiments, the amount of wax present in the formulation is greater than 10 micrograms/mL and less than 50 mg/mL. In some embodiments, the wax is present in at least 0.03 mg/mL in the final formulation.

In some embodiments, the natural carbon dioxide cannabis extract has <10 ppm of residual solvent. In some embodiments, the solvent comprises an amount of ethanol, methanol, butane, acetone, propane, hexane, heptane, pentane, chloroform, octane, benzene, toluene, methyl tert-butyl ether, ethyl tert-butyl ether, methylene chloride chloromethane and/or isopropanol. In some embodiments, the ethanol is present in an amount of up to 30% w/w, for example, up to 5, 10, 15, 20, 25, or 30% w/w.

A variety of propellants can be employed in various embodiments. In some embodiments, the propellant comprises at least a HFA. In some embodiments, the HFA is at least one of 1,1,1,2-Tetrafluoroethane (HFA 134a) and 1,1,1,2,3,3,3-Heptafluoropropane (HFA 227). In other embodiments, alternative solvents can be employed.

In some embodiments, the formulation further comprises a surfactant. In some embodiments, the surfactant is present in an amount adequate for improving solubility. In some embodiments, the surfactant is present in an amount of up to 10% w/w. In some embodiments, the surfactant comprises oleic acid. In some embodiments, additional or alternative surfactants can be applied if confirmed for the uses as provided herein.

In some embodiments, a formulation for a metered dose inhalation is provided. The formulation can comprise an amount of an activated cannabinoid, wherein the activated cannabinoid comprises at least Tetrahydrocannabinol (THC) and Cannabidiol (CBD), an amount of ethanol sufficient to serve as a solvent, and an amount of a propellant, wherein the propellant is at least one of 1,1,1,2-Tetrafluoroethane (HFA 134a) and 1,1,1,2,3,3,3-Heptafluoropropane (HFA 227). The formulation can also include at least one of: a) an amount of a wax, wherein the amount of wax is at least sufficient to provide a higher level of comfort to a subject receiving a dose from a metered dose inhaler that is administering the formulation, and wherein the wax comprises a wax that naturally occurs in a cannabis plant, or b) an amount of a natural terpene. The natural terpene is one that is present in a cannabis plant, and wherein the amount of the natural terpene is at least sufficient to provide a higher level of comfort to a subject receiving a dose from a metered dose inhaler that is administering the formulation. In some embodiments, the wax is one that is natural to a cannabis plant, but is not removed fully during the processing of the cannabis plant.

In some embodiments, a formulation for metered dose inhalation is provided. In some embodiments, the formulation can comprise 1) an amount of an extract from a cannabinoid containing plant. The extract can comprise an activated cannabinoid, wherein the activated cannabinoid comprises at least Tetrahydrocannabinol (THC) and Cannabidiol (CBD). The formulation can further include at least one of: i) an amount of a wax, wherein the amount of wax is at least sufficient to provide a higher level of comfort to a subject receiving a dose from a metered dose inhaler that is administering the formulation, and wherein the wax comprises a wax that naturally occurs in a cannabis plant, or ii) an amount of a natural terpene. The natural terpene can be one that is present in a cannabis plant. The amount of the natural terpene and/or the natural wax is at least sufficient to provide a higher level of comfort to a subject receiving a dose from a metered dose inhaler that is administering the formulation. The formulation can further include 2) an amount of a polar solvent; and 3) an amount of a HFA propellant, wherein the propellant is at least one of 1,1,1,2-Tetrafluoroethane (HFA 134a) and 1,1,1,2,3,3,3-Heptafluoropropane (HFA 227). In some embodiments, the extract:polar solvent:HFA propellant is in a ratio ranging from about 0.5:0.5:99 to about 30:30:40. In some embodiments, the formulation further includes a surfactant at up to 10% w/w.

In some embodiments, the formulation further comprises Cannabidiol (CBD) and further comprises nicotine. In some embodiments, the formulation comprises nicotine.

In some embodiments, any one of the formulations provided herein can be configured for nasal delivery. In some embodiments, a satisfactory amount of the desired ingredients is effectively administered through the nose by such a formulation.

Metered Dose Inhaler

In some embodiments, a metered dose inhaler 80 is provided for the delivery of any of the formulations provided herein, or for the delivery of other metered dose inhaler formulations. The MDI 80 can include any standard component for a MDI. In some embodiments, it will include a chamber 50, configured for receiving the canister that contains the formulation, an actuator 70, which can include a valve mating boss 75 for the canister, a channel 12 which allows the formulation from the canister to pass through it, through the jet 11, out an orifice 21 of the actuator (or actuator orifice), through the opening for the mouth piece 30, to pass out of the mouth piece itself (not shown). The outer wall 40 of the MDI can form the mouthpiece and the chamber 50.

In some embodiments, altering the jet length 10 and/or the actuator orifice diameter 20 can result in a more desirable experience for the user for receiving the formulation. In some embodiments, any of the formulations provided herein can be applied in the device of FIG. 1.

In some embodiments, the metered dose inhaler comprises a formulation as provided herein and an actuator drug/propellant pathway, that includes an actuator orifice 21 configured to provide an appropriate mean mass aerosol diameter (MMAD) particulate size distribution (between 0.5 and 5.0 micron) of the cannabis formulation, and of sufficient surface area and heat sink properties to provide for single and rapid dispensing cycles of the formulation (including propellant) to maintain dose content uniformity, particle size distribution, and the comfort of the subject. In some embodiments, the actuator orifice 21 is configured by at least one of an appropriate surface area (Pi×Jet Length×Orifice diameter), internal geometry "jet length," shape, surface texture, or material, of the actuator orifice.

In some embodiments, the configuration denotes an increased mass of the external geometry of the actuator structure to act as a heat sink. In some embodiments, this is at least 5% additional mass beyond a traditional device. In some embodiments, this is at least 5, 7, 8, 9, 10, 20, 30, 40, 50, 60, 70, 80, 90, 100, 200, 300, 400, 500, 600, 700, 800, 900, or 1000% more mass. Some embodiments of the areas and shapes of the additional mass are shown as item **22*a*-22*c* in FIG. 1. In some embodiments, all three areas can employ additional mass. In some embodiments, the area 22*a* beneath the orifice 21 can employ the additional mass. In some embodiments, the area 22*b* above the orifice 21 can employ the additional mass. In some embodiments the area 22*c* behind the orifice 21** can employ the additional mass.

In some embodiments, the checkerboard pattern on FIG. 1 represents options to increase this mass by introducing a cone shape as opposed to a cylinder shape, adding between 0 and 50% to the mass of the valve stem mating boss 75. In some embodiments, the valve stem mating boss is not cylindrical, so that additional mass can be added. In some embodiments, it is cone shaped. In some embodiments, the valve stem mating boss is at least 5, 7, 8, 9, 10, 20, 30, 40, 50, 60, 70, 80, 90, 100, 200, 300, 400, 500, 600, 700, 800, 900, or 1000% more mass than a normal valve stem mating boss (the candy striped section depicted in FIG. 1). In some embodiments, the valve stem mating boss weighs as least 50 mg and less than 5 grams. In some embodiments, the valve stem mating boss 75. has a higher volume than a traditional valve stem mating boss, for example 10, 20, 30, 40, 50, 100, 200, 300, 400, 500, or greater percent increase in volume compared to traditional valve stem mating bosses. In some embodiments, the range of volumes can be 0.15 cm$^3$ to 2.5 cm$^3$.

In some embodiments, the increased surface area is achieved by increasing the jet length 10 of the cylinder or a shape of the actuator orifice outlet 21.

In some embodiments, the increased surface area is achieved by increasing the texture of the cylinder area by using cuts, grooves, ridges, or by using a mold etched texture such as Mold-Tech MT-11200 of the path through which the formulation passes (from the valve mating boss 75 through to the orifice 21. Thus, in some embodiments, the channel 12 and/or jet 11 can include any additional structural feature so as to increase the surface area of the flow path of the formulation. In some embodiments, the flow path (the path between the valve mating boss and the orifice diameter, is not smooth. In some embodiments, the flow path from the orifice to the exit in the mouth piece is also configured so as to provide an increase in surface area interaction of the formulation with the device. As such, the increased surface area achieved by increasing the texture by using cuts, grooves, ridges, or by using a mold etched texture can also be applied to the interior surface of the outer walls of the MDI 40, in the area of the opening for the mouth piece 30.

In some embodiments, the orifice diameter 20 of the orifice 21 is about 0.15 mm to 0.65 mm, for example 0.2, 0.3, 0.4, 0.5. 0.6, or 0.65 mm, including any range defined between any two of the previous values. In some embodiments, the orifice diameter is greater than 0.3 mm. In some embodiments, the orifice diameter is between 0.3 and 0.7 mm, for example, 0.31, 0.35, 0.4, 0.45, 0.5, 0.55, 0.6, 0.65, or 0.7, including any range defined between any two of the preceding values.

In some embodiments, the actuator jet length has a length of 0.15 to 2.50 mm, for example, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, or 2.5 mm, including any range defined between any two of the previous values.

In some embodiments, a MDI valve is located between the MDI canister and the valve mating boss 75, wherein the MDI valve is configured to dispense between 25 and 125 microliters of formulation per actuation, and wherein the MDI valve is made of at least one of polyoxymethalate (POM), polybutylterephalate (PBT), ABS, acrylic, polycarbonate, ethylene propylene diene monomer (EPDM), or silicon. In some embodiments, a MDI valve is located between the MDI canister and the valve mating boss 75, wherein the MDI valve is configured to dispense between 20 and 125 microliters of formulation per actuation, and wherein the MDI valve is made of at least one of polyoxymethalate (POM), polybutylterephalate (PBT), ABS, acrylic, polycarbonate, ethylene propylene diene monomer (EPDM), or silicon.

In some embodiments, a MDI canister is provided that can include any of the formulations provided herein and a coating over an interior surface of the canister. The coating can be one to increase the level of comfort to a subject to which the formulation is administered. In some embodiments, the coating can alter the taste and/or prevent the taste of the formulation from being altered from storage/exposure to the interior of the canister. In some embodiments, the coating comprises at least one of anodized aluminum or a fluoropolymer. In some embodiments, the fluoropolymer has either been sprayed on the interior surface or deposited via plasma deposition. In some embodiments, the canister further comprises a MDI valve that is configured to dispense between 25 and 125 microliters of formulation per actuation. In some embodiments, the MDI valve comprises at least one of polyoxymethalate (POM), polybutylterephalate (PBT), ABS, acrylic, polycarbonate, ethylene propylene diene monomer (EPDM), and silicon.

By increased "comfort" what is denoted is that the subject feels less discomfort from the inhalation of the formulation, in comparison to when the aspect is absent. In some embodiments, this indicates that the level of comfort is closer to the sensation of normal breathing. In some embodiments, this indicates that the inhaled formulation feels warmer or is less cold, bright or sharp when inhaled. In some embodiments, comfort will be increased due to a less cold spray. In some embodiments, this will be more evident with more rapid dosing as subsequent doses will not get as progressively colder as an unmodified system.

Manufacturing

In some embodiments, the extract containing the cannabinoid can be decarboxylated by immersion in an oil bath. In some embodiments, this occurs at above 100 degrees centigrade for an adequate amount of time. In some embodiments, this occurs for 155 degrees centigrade for 80 minutes.

In some embodiments, the extract can then be mixed an organic solvent. In some embodiments, this can be alcohol. In some embodiments, it is 200 Proof USP grade ethanol. In some embodiments, this can be at a ratio of 37:63 extract to ethanol. Dissolution of the extract can be achieved by agitation and heating. In some embodiments, this can be heated to as much as 78 degrees Centigrade (boiling point of ethanol) to fully dissolve the extract. The sample is then cooled. In some embodiments, it is cooled to 5 degrees centigrade to form a gel phase. In some embodiments, this can be employed in a suitable MDI canister. The canister is crimped with a suitable valve and charged with 134a (or 227ea) by over pressure through the valvestem. The canister is agitated by hand for no less than 10 seconds.

In some embodiments, a method for preparing a formulation is provided. The method can include providing a source of a cannabinoid. The method can further include obtaining an active ingredient from the source by carbon dioxide extraction. The method can further include combining the active ingredient with a polar solvent to obtain a mixture. The method can further include heating the mixture to solubilize it into a solvent. The method can further include cooling the solvent to thereby obtain a gel or viscous liquid and solubilizing the gel or viscous liquid with HFA.

In some embodiments, the formulation is prepared by preparing the extract in separate fractions. In some embodiments, heating comprises extracting at least one of THC or CBD via an oil bath.

EXAMPLE 1

Manufacturing

An extract containing a cannabinoid is obtained by $CO_2$ extraction. The extract containing the cannabinoid will then be decarboxylated by immersion in an oil bath for 155 degrees centigrade for 80 minutes. The extract will then be mixed with 200 Proof USP grade ethanol in a ratio of 37:63 extract to ethanol. Dissolution of the extract will be achieved by agitation and heating to as much as 78 degrees centigrade (boiling point of ethanol) to fully dissolve the extract.

Upon to cooling to 5 C a gel phase will be formed.

EXAMPLE 2

The gel phase from example 1 will be filled into a suitable MDI canister that has an anodized interior coating over it. The canister will then be crimped with a suitable valve and charged with 134a (or 227ea) by over pressure through the valvestem. The canister will then be agitated by hand for no less than 10 seconds.

EXAMPLE 3

The canister from Example 2 is inserted into the MDI of FIG. 1. A subject to receive a formulation as described herein depresses the canister to actuate it, delivering the formulation to the subject. The subject experiences less discomfort than if the subject had applied a formulation lacking wax and/or terpenes in an adequate amount and/or if a traditional MDI device had been employed (as shown in FIG. 1, but lacking structures 22a, 22b, or 22c, or having a typical jet length or a typical orifice diameter).

EXAMPLE 4

An extract containing a cannabinoid is obtained by $CO_2$ extraction. The extract containing the cannabinoid will then be decarboxylated by immersion in an oil bath for 155 degrees centigrade for 80 minutes. The extract will then be mixed with 200 Proof USP grade ethanol in a mass ratio of 50:50 extract to ethanol. Dissolution of the extract will be achieved by agitation and heating to as much as 78 degrees centigrade (boiling point of ethanol) to fully dissolve the extract.

Upon to cooling to 5 C a gel phase will be formed.

Although the present application has been described in detail above, it will be understood by one of ordinary skill in the art that various modifications can be made without departing from the spirit of the invention. Accordingly, the present application is limited only by the following claims. All cited patents, patent applications and publications referred to in this application are herein incorporated by reference in their entirety. In this application, the use of the singular can include the plural unless specifically stated otherwise or unless, as will be understood by one of skill in the art in light of the present disclosure, the singular is the only functional embodiment. Thus, for example, "a" can mean more than one, and "one embodiment" can mean that the description applies to multiple embodiments. Additionally, in this application, "and/or" denotes that both the inclusive meaning of "and" and, alternatively, the exclusive meaning of "or" applies to the list. Thus, the listing should be read to include all possible combinations of the items of the list and to also include each item, exclusively, from the other items. The addition of this term is not meant to denote any particular meaning to the use of the terms "and" or "or" alone. The meaning of such terms will be evident to one of skill in the art upon reading the particular disclosure. All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls. The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof. As will be appreciated by one of skill in the art, while the present specification may simply use one of the terms "comprise," "consists," or "consists essentially of," this is simply a shorthand way of describing all three possibilities, unless otherwise specified or unless the term is used in the claim (in which case the terms will have their normally accepted meanings under claim interpretation). Thus, as the terms are used above, they designate all three possibilities, unless explicitly noted otherwise.

What is claimed is:

1. A formulation for metered dose inhalation, said formulation comprising:
    an extract comprising an amount of at least one cannabinoid, wherein the at least one cannabinoid comprises a cannabidiol (CBD), and wherein the amount of the at least one cannabidiol is at least 0.2 mg/mL and less than 350 mg/mL;
    an amount of a propellant suitable for metered dose inhalation application to a human subject, wherein the propellant comprises at least a HFA;
    a polar solvent;
    an amount of a wax, wherein the wax is present in an amount of greater than 10 µg/mL and less than 50 mg/mL;
    wherein the polar solvent is miscible with the propellant, the cannabinoid(s), and the wax, wherein extract: polar solvent: HFA propellant is in a ratio ranging from 0.5:0.5:99 to 30:30:40; and
    a terpene, in an amount of at least 3 µg/mL.

2. The formulation of claim 1, wherein the wax comprises a plant based natural wax.

3. The formulation of claim 2, wherein the plant based natural wax comprises a cannabis wax.

4. The formulation of claim 2, wherein the plant based natural wax comprises a non-cannabis wax.

5. The formulation of claim 1, wherein the terpene is selected from the group of at least one of: Pinene, Limonene, Myreene, Pheilandrene, Carene, Terpinene, Linalool, Fenchol, Borneol, Terpineol, Geraniol, Humulene, Caryophyllene, Caryophyllene Oxide, Bisabolol, Citronellal, Menthol, Ocimene, Camphene or Phytol.

6. The formulation of claim 1, wherein the at least one cannabinoid further comprises at least one activated cannabinoid.

7. The formulation of claim 1, wherein the at least one cannabinoid further comprises at least one cannabinoid selected from the group of at least Tetrahydrocannabinol (THC), and Tetrahydrocannabivarin (THCV).

8. The formulation of claim 1, wherein the at least one cannabinoid further comprises THC.

9. The formulation of claim 1 wherein the wax is present in an amount of at least 0.03 mg/mL.

10. The formulation of claim 1, wherein the solvent comprises an amount of ethanol.

11. The formulation of claim 10, where the ethanol is present in an amount of up to 30% w/w.

12. The formulation of claim 1, wherein the HFA is at least one of 1,1,1,2-Tetrafluoroethane (HFA 134a) and 1,1,1,2,3,3,3-Heptafluoropropane (HFA 227ca).

13. A formulation for metered dose inhalation, said formulation comprising:
an amount of an activated cannabinoid, wherein the activated cannabinoid comprises at least Tetrahydrocannabinol (THC) and Cannabidiol (CBD), wherein the amount of the Cannabidiol is at least 0.2 mg/mL and less than 350 mg/mL;
an amount of ethanol sufficient to serve as a solvent; an amount of a propellant, wherein the propellant is at least one of 1,1,1,2- Tetrafluoroethane (HFA 134a) and 1,1,1,2,3,3,3-Heptafluoropropane (HFA 227ea), wherein an extract comprises the activated cannabinoid,
an amount of a wax, in an amount of greater than 10 µg/mL and less than 50 mg/mL, wherein the wax comprises a wax that naturally occurs in a cannabis plant, and
an amount of a natural terpene, in an amount of at least 3 µg/mL, wherein the natural terpene is one that is present in a cannabis plant, and wherein the amount of the natural terpene is at least sufficient to provide a higher level of comfort to a subject receiving a close from a metered dose inhaler that is administering the formulation,
wherein extract:ethanol:IFA propellant is in a ratio ranging from 0.5:0.5:99 to 30:30:40.

14. A metered dose inhaler canister comprising:
a formulation according to claim 13; and
a coating over an interior surface of the canister, wherein the coating comprises at least one of anodized aluminum or a fluoropolymer.

15. A metered dose inhaler comprising:
a formulation according to claim 13; and
an actuator drug/propellant pathway, comprising an actuator orifice cylinder configured to provide an appropriate mean mass aerosol diameter (MMAD) particulate size distribution of the formulation, and of sufficient surface area and heat sink properties to provide for single and rapid dispensing cycles of the formulation, and propellant, to maintain dose content uniformity, particle size distribution, and the comfort of the patient; wherein the actuator orifice cylinder is configured by at least one of:
a) an appropriate surface area, internal geometry jet length or shape, surface texture, or material of the actuator orifice cylinder; or
b) an increased mass of the external geometry of the actuator orifice cylinder, as compared to the mass of the external geometry of the actuator orifice cylinder without a heat sink, to act as a heat sink by at least 5% additional mass.

16. The metered dose inhaler of claim 15, wherein an increased surface area, as compared to the surface area of the external geometry of the actuator orifice cylinder without a heat sink, is achieved by increasing the texture of the cylinder area by at least one of a cut, a groove, a ridge, or by a mold etched texture.

17. The metered dose inhaler of claim 15, wherein a MDI valve is located between the MDI canister and the orifice cylinder, wherein the MDI valve is configured to dispense between 20 and 125 microliters of formulation per actuation, and wherein the MDI valve is made of at least one of polyoxymethalate (POM), polybutylterephalate (PBT), ABS, acrylic, polycarbonate, ethylene propylene diene monomer (EPDM), or silicon.

18. The metered dose inhaler of claim 15, wherein the appropriate mean mass aerosol diameter (MMAD) particulate size distribution is between 0.5 and 5.0 micron of the formulation.

19. The formulation of claim 12, wherein the wax, CBD, and terpene are from the extract,
wherein the extract is plant based, and
wherein the solvent is ethanol, and wherein the ethanol is present in an amount of up to 30% w/w.

* * * * *